United States Patent
Lichtenstein

(10) Patent No.: US 11,207,125 B2
(45) Date of Patent: *Dec. 28, 2021

(54) EFFECTIVE PARASITIC CAPACITANCE MINIMIZATION FOR MICRO ABLATION ELECTRODE

(71) Applicant: BIOSENSE WEBSTER (ISRAEL) LTD., Yokneam (IL)

(72) Inventor: Yoav Lichtenstein, Raanana (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/889,594

(22) Filed: Jun. 1, 2020

(65) Prior Publication Data
US 2020/0289187 A1 Sep. 17, 2020

Related U.S. Application Data

(62) Division of application No. 14/850,212, filed on Sep. 10, 2015, now Pat. No. 10,709,492.

(Continued)

(51) Int. Cl.
*A61B 18/14* (2006.01)
*A61B 18/12* (2006.01)
(Continued)

(52) U.S. Cl.
CPC ...... *A61B 18/1206* (2013.01); *A61B 18/1492* (2013.01); *A61B 5/30* (2021.01);
(Continued)

(58) Field of Classification Search
CPC ........ A61B 5/0428; A61B 2018/00029; A61B 2018/00351; A61B 2018/00577;
(Continued)

(56) References Cited

U.S. PATENT DOCUMENTS 5,515,848 A * 5/1996 Corbett, III ............. A61F 11/04
600/377
6,226,542 B1 5/2001 Reisfeld
(Continued)

FOREIGN PATENT DOCUMENTS

AU 2015202245 A1 12/2015
AU 2015202245 B2 7/2019
(Continued)

OTHER PUBLICATIONS

European Search Report dated Mar. 18, 2016 from corresponding European Patent Application No. 15189481.3.
(Continued)

*Primary Examiner* — Jaymi E Della

(57) ABSTRACT

A flexible catheter has an ablation electrode disposed in its distal segment. The ablation electrode a cavity formed in its external surface, a microelectrode configured to fit into the cavity, a conductive wire lead connecting the microelectrode to receiving circuitry, and an electrical shield surrounding the wire lead. A power generator is connected to the ablation electrode and the electrical shield in a generator circuit. A back patch electrode adapted to contact with the subject is connected in the generator circuit. The microelectrodes can be active while energizing the ablation electrode.

8 Claims, 4 Drawing Sheets

Related U.S. Application Data

(60) Provisional application No. 62/063,456, filed on Oct. 14, 2014.

(51) Int. Cl.
   *A61B 18/00* (2006.01)
   *A61B 18/16* (2006.01)
   *A61B 5/30* (2021.01)

(52) U.S. Cl.
   CPC . *A61B 18/1233* (2013.01); *A61B 2018/00029* (2013.01); *A61B 2018/00351* (2013.01); *A61B 2018/00577* (2013.01); *A61B 2018/00821* (2013.01); *A61B 2018/00839* (2013.01); *A61B 2018/1467* (2013.01); *A61B 2018/167* (2013.01); *A61B 2218/002* (2013.01)

(58) Field of Classification Search
   CPC ........... A61B 2018/00821; A61B 2018/00839; A61B 2018/1467; A61B 2018/167; A61B 2218/002; A61B 18/1492; A61B 18/1206
   See application file for complete search history.

(56) References Cited

U.S. PATENT DOCUMENTS

| | | |
|---|---|---|
| 6,301,496 B1 | 10/2001 | Reisfeld |
| 6,814,733 B2 | 11/2004 | Schwartz |
| 6,892,091 B1 | 5/2005 | Ben-Haim |
| 6,997,924 B2 | 2/2006 | Schwartz |
| 7,156,816 B2 | 1/2007 | Schwartz |
| 7,536,218 B2 | 5/2009 | Govari |
| 7,756,576 B2 | 7/2010 | Levin |
| 9,662,170 B2 | 5/2017 | Budzelaar |
| 2008/0243214 A1* | 10/2008 | Koblish ............. A61B 18/1492 600/374 |
| 2011/0202051 A1* | 8/2011 | Hagg ................. A61B 18/1402 606/35 |
| 2013/0190747 A1 | 7/2013 | Koblish |
| 2013/0324993 A1 | 12/2013 | McCarthy |
| 2014/0058375 A1 | 2/2014 | Koblish |
| 2014/0155758 A1 | 6/2014 | Brichard |
| 2015/0327921 A1 | 11/2015 | Govari |

FOREIGN PATENT DOCUMENTS

| | | |
|---|---|---|
| CN | 103220983 A | 7/2013 |
| CN | 103220983 B | 12/2015 |
| EP | 2944282 A1 | 11/2015 |
| WO | WO2012066446 A1 | 5/2012 |
| WO | WO2014072879 A2 | 5/2014 |
| WO | WO2014072879 A3 | 9/2014 |
| WO | WO2014152575 A2 | 9/2014 |
| WO | WO2014163990 A1 | 10/2014 |

OTHER PUBLICATIONS

Examination Search Report No. 1 dated Jul. 24, 2019 from corresponding Australian Patent Application No. 2015238802, pp. 4.
Japanese Notification of Reason for Refusal for application No. 2015-201784, dated Jul. 24, 2019, pp. 5.
Chinese First Office Action for application No. CN201510663286.6, dated Mar. 7, 2019, pp. 12.

* cited by examiner

EFFECTIVE PARASITIC CAPACITANCE MINIMIZATION FOR MICRO ABLATION ELECTRODE

CROSS-REFERENCE TO RELATED APPLICATIONS

This application is a divisional of application Ser. No. 14/850,212, filed Sep. 10, 2015, now U.S. Pat. No. 10,709,492 which claims the benefit of Provisional Application Ser. No. 62/063,456 filed Oct. 14, 2014, which is herein incorporated by reference.

BACKGROUND OF THE INVENTION

1. Field of the Invention

This invention relates to medical instruments for electrical application to the body. More particularly, this invention relates to improvements in medical ablation catheters.

2. Description of the Related Art

Radiofrequency (RF) ablation of the heart is a procedure that is widely used to correct problematic cardiac conditions, such as atrial fibrillation. The procedure typically involves insertion of a catheter having an electrode into the heart, and ablating selected regions within the heart with RF energy transmitted via the electrode. Capacitive effects can interfere with electrophysiologic signals when power is transmitted to an ablation electrode.

U.S. Patent Application Publication No. 2014/0155758, entitled Low Capacitance Endoscopic System proposes an endoscopic system having distal sensors, in which the capacitance of the sensor system relative to earth ground maintains current leakage to a level that meets a cardiac float rating. During sensing, power can be transmitted to the sensor via a power transmission line from a groundreferenced power source, and data signals can be transmitted to the sensor via a data signal transmission line from a processing circuit at a proximate end of the endoscopic shaft. In response to electromagnetic interference proximate the remote surgical site, induced voltages level changes in the data signal transmission line and the power transmission are substantially equalized.

Arrangements wherein an ablation electrode in the catheter is in proximity to microelectrodes are known, for example, from U.S. Patent Application Publication No. 2013/0190747, which discloses an ablation catheter having a tissue ablation electrode and a plurality of microelectrodes distributed about the circumference of the tissue ablation electrode and electrically isolated therefrom. The plurality of microelectrodes define a plurality of bipolar microelectrode pairs. In this arrangement mapping microelectrodes are disposed near the ablation tip electrode to allow the center of mapping or pacing to be in substantially the same location as the center of ablation. It is asserted that the microelectrodes can advantageously provide feedback on electrode contact and tip electrode orientation within the heart.

SUMMARY OF THE INVENTION

There is provided according to embodiments of the invention an apparatus including a flexible catheter adapted for insertion into a heart of a living subject, an ablation electrode disposed at the distal segment of the catheter to be brought into contact with a target tissue in the heart. The ablation electrode has a cavity formed in its external surface, a microelectrode configured to fit into the cavity, a conductive wire lead connecting the microelectrode to receiving circuitry, and an electrical shield surrounding the wire lead.

A further aspect of the apparatus includes a generator circuit connecting a power generator to the ablation electrode and the electrical shield, and a back patch electrode adapted to contact with the subject and connected in the generator circuit.

According to another aspect of the apparatus, the electrical shield includes a coaxial layer, and a dielectric layer disposed between the coaxial layer and the wire lead.

According to one aspect of the apparatus, the electrical shield also includes an insulating jacket that overlies the coaxial layer.

According to a further aspect of the apparatus the microelectrode is contoured, located and oriented to conform to a curvature of the ablation electrode.

According to yet another aspect of the apparatus, the ablation electrode has a cylindrical portion, wherein the cavity includes a plurality of cavities formed in the cylindrical portion.

According to still another aspect of the apparatus, the ablation electrode has a distal annular portion, wherein the cavity includes a plurality of cavities formed in the annular portion and a plurality of microelectrodes disposed therein.

According to an additional aspect of the apparatus, the microelectrode is linked to a thermocouple that provides a signal representative of a temperature of the microelectrode.

There is further provided according to embodiments of the invention a method, which is carried out by inserting a flexible catheter into a heart of a living subject. The catheter has an ablation electrode disposed at the distal segment of the catheter. A cavity is formed in the external surface ablation electrode and a microelectrode fitted into the cavity. A conductive wire lead connects the microelectrode and receiving circuitry. An electrical shield surrounds the wire lead. A power generator connects the ablation electrode and the electrical shield in a generator circuit. The method is further carried out by connecting a back patch electrode to the subject and to the generator circuit. The method is further carried out by contacting the ablation electrode with a target tissue in the heart, and while receiving signals from the microelectrode in the receiving circuitry energizing the ablation electrode to ablate the target tissue.

BRIEF DESCRIPTION OF THE SEVERAL VIEWS OF THE DRAWINGS

For a better understanding of the present invention, reference is made to the detailed description of the invention, by way of example, which is to be read in conjunction with the following drawings, wherein like elements are given like reference numerals, and wherein.

DETAILED DESCRIPTION OF THE INVENTION

In the following description, numerous specific details are set forth in order to provide a thorough understanding of the various principles of the present invention. It will be apparent to one skilled in the art, however, that not all these details are necessarily needed for practicing the present invention. In this instance, well-known circuits, control logic, and the details of computer program instructions for conventional algorithms and processes have not been shown in detail in order not to obscure the general concepts unnecessarily.

Documents incorporated by reference herein are to be considered an integral part of the application except that, to the extent that any terms are defined in these incorporated documents in a manner that conflicts with definitions made explicitly or implicitly in the present specification, only the definitions in the present specification should be considered.

The terms "link", "links", "couple" and "couples" are intended to mean either an indirect or direct connection. Thus, if a first device is linked to a second device, that connection may be through a direct connection, or through an indirect connection via other devices and connections.
Overview.

Figure 1:
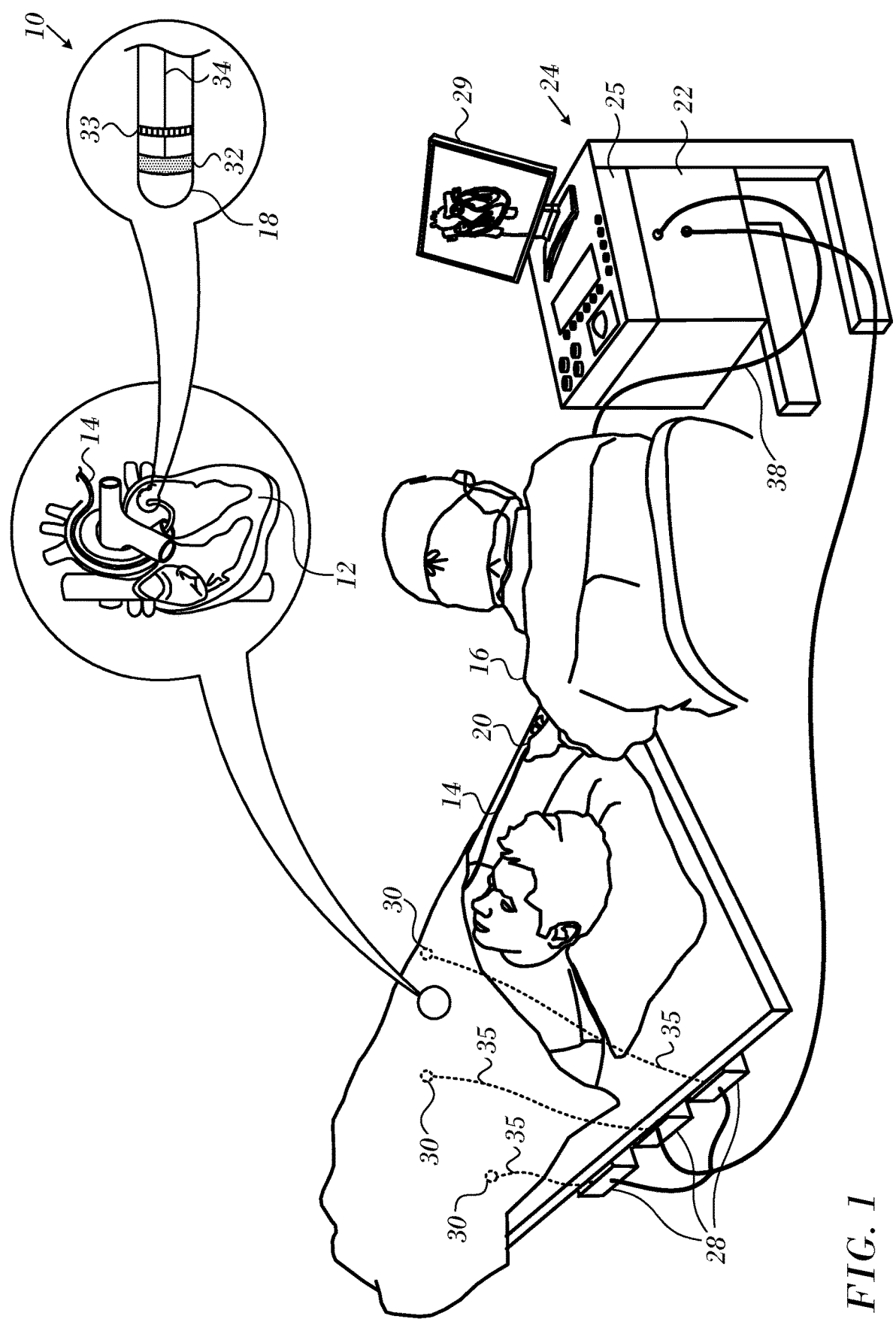
FIG. 1 is a pictorial illustration of a system, which is constructed and operative in accordance with a disclosed embodiment of the invention.

Turning now to the drawings, reference is initially made to FIG. 1, which is a pictorial illustration of a system 10 for evaluating electrical activity and performing ablative procedures on a heart 12 of a living subject, which is constructed and operative in accordance with a disclosed embodiment of the invention. The system comprises a catheter 14, which is percutaneously inserted by an operator 16 through the patient's vascular system into a chamber or vascular structure of the heart 12. The operator 16, who is typically a physician, brings the catheter's distal tip 18 into contact with the heart wall, for example, at an ablation target site. Electrical activation maps may be prepared, according to the methods disclosed in U.S. Pat. Nos. 6,226,542, and 6,301,496, and in commonly assigned U.S. Pat. No. 6,892,091, whose disclosures are herein incorporated by reference. One commercial product embodying elements of the system 10 is available as the CARTO® 3 System, available from Biosense Webster, Inc., 3333 Diamond Canyon Road, Diamond Bar, Calif. 91765. This system may be modified by those skilled in the art to embody the principles of the invention described herein.

Areas determined to be abnormal, for example by evaluation of the electrical activation maps, can be ablated by application of thermal energy, e.g., by passage of radiofrequency electrical current through wires in the catheter to one or more electrodes at the distal tip 18, which apply the radiofrequency energy to the myocardium. The energy is absorbed in the tissue, heating it to a point (typically about 50° C.) at which it permanently loses its electrical excitability. When successful, this procedure creates non-conducting lesions in the cardiac tissue, which disrupt the abnormal electrical pathway causing the arrhythmia. The principles of the invention can be applied to different heart chambers to diagnose and treat many different cardiac arrhythmias.

The catheter 14 typically comprises a handle 20, having suitable controls on the handle to enable the operator 16 to steer, position and orient the distal end of the catheter as desired for the ablation. To aid the operator 16, the distal portion of the catheter 14 contains position sensors (not shown) that provide signals to a processor 22, located in a console 24. The processor 22 may fulfill several processing functions as described below.

Ablation energy and electrical signals can be conveyed to and from the heart 12 through one or more ablation electrodes 32 located at or near the distal tip 18 via cable 34 to the console 24. Pacing signals and other control signals may be conveyed from the console 24 through the cable 34 and the electrodes 32 to the heart 12. Sensing electrodes 33, also connected to the console 24 are disposed between the ablation electrodes 32 and have connections to the cable 34.

Wire connections 35 link the console 24 with body surface electrodes 30 and other components of a positioning sub-system for measuring location and orientation coordinates of the catheter 14. The processor 22 or another processor (not shown) may be an element of the positioning subsystem. The electrodes 32 and the body surface electrodes 30 may be used to measure tissue impedance at the ablation site as taught in U.S. Pat. No. 7,536,218, issued to Govari et al., which is herein incorporated by reference. A temperature sensor (not shown), typically a thermocouple or thermistor, may be mounted on or near each of the electrodes 32.

The console 24 typically contains one or more ablation power generators 25. The catheter 14 may be adapted to conduct ablative energy to the heart using any known ablation technique, e.g., radiofrequency energy, ultrasound energy, and laser-produced light energy. Such methods are disclosed in commonly assigned U.S. Pat. Nos. 6,814,733, 6,997,924, and 7,156,816, which are herein incorporated by reference.

In one embodiment, the positioning subsystem comprises a magnetic position tracking arrangement that determines the position and orientation of the catheter 14 by generating magnetic fields in a predefined working volume and sensing these fields at the catheter, using field generating coils 28. The positioning subsystem U.S. Pat. No. 7,756,576, which is hereby incorporated by reference, and in the above-noted U.S. Pat. No. 7,536,218.

As noted above, the catheter 14 is coupled to the console 24, which enables the operator 16 to observe and regulate the functions of the catheter 14. Console 24 includes a processor, preferably a computer with appropriate signal processing circuits. The processor is coupled to drive a monitor 29. The signal processing circuits typically receive, amplify, filter and digitize signals from the catheter 14, including signals generated by sensors such as electrical, temperature and contact force sensors, and a plurality of location sensing electrodes (not shown) located distally in the catheter 14. The digitized signals are received and used by the console 24 and the positioning system to compute the position and orientation of the catheter 14, and to analyze the electrical signals from the electrodes.

Typically, the system 10 includes other elements, which are not shown in the figures for the sake of simplicity. For example, the system 10 may include an electrocardiogram (ECG) monitor, coupled to receive signals from one or more body surface electrodes, in order to provide an ECG synchronization signal to the console 24. As mentioned above, the system 10 typically also includes a reference position sensor, either on an externally-applied reference patch attached to the exterior of the subject's body, or on an internally-placed catheter, which is inserted into the heart 12 maintained in a fixed position relative to the heart 12. Conventional pumps and lines for circulating liquids through the catheter 14 for cooling the ablation site are provided. The system 10 may receive image data from an external imaging modality, such as an MRI unit or the like and includes image processors that can be incorporated in or invoked by the processor 22 for generating and displaying images.

Microelectrode Catheter Tip.

Figure 2:
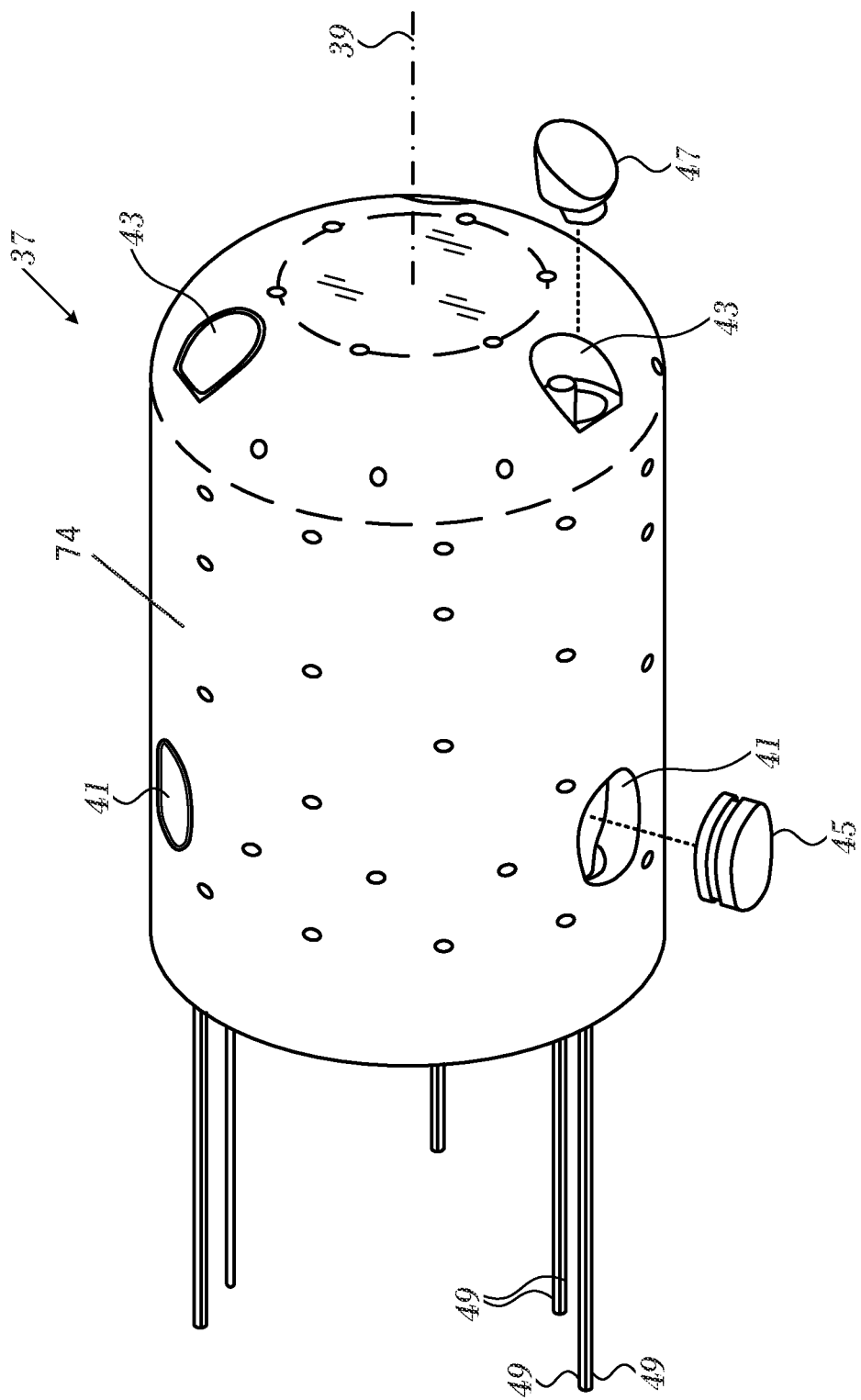
FIG. 2 is a schematic diagram illustrating assembly of distal end of a catheter in accordance with an embodiment of the invention.

Reference is now made to FIG. 2, which is a schematic diagram illustrating an assembly of distal end 37 of a catheter in accordance with an embodiment of the invention. An isolated guard shield is placed over the microelectrode wires and connected to an ablation electrode to equalize potentials. This arrangement minimizes stray capacitance that may conduct current to other shaft electrodes or to system ground. An insertion tube terminates in the distal end 37, which is formed from a biocompatible conductor, such as platinum, palladium, gold, iridium, or an alloy of the aforementioned, and which has an axis of symmetry 39. At least one cavity 41 is formed in the cylindrical region of external surface 74, and at least one cavity 43 is formed in the curved annular region of the external surface. The embodiment described herein comprises three cavities 41, which are distributed symmetrically with respect to axis of symmetry 39, and three cavities 43 are also distributed symmetrically with respect to the axis of symmetry 39. However, these numbers and distributions are purely by way of example. Embodiments of the present invention may have different numbers of cavities, and different distributions of the cavities, from those described herein. As described below, each cavity 41 is configured to accept and mate with a respective microelectrode 45 and each cavity 43 is configured to accept and mate with a respective microelectrode 47.

Figure 3:
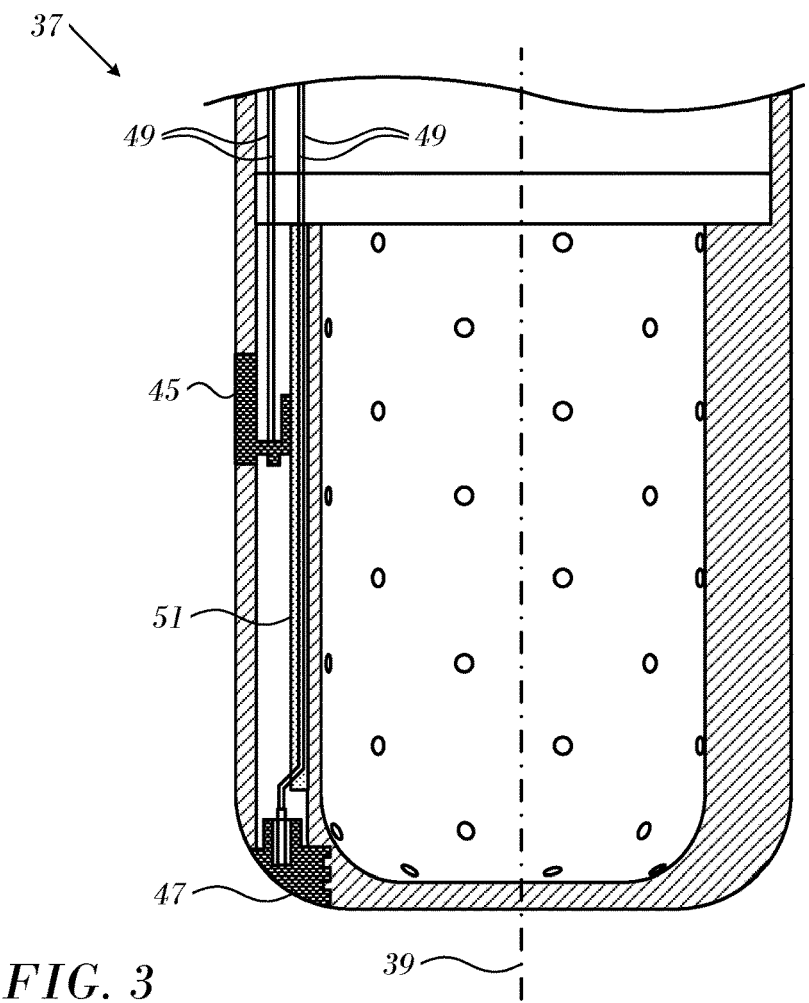
FIG. 3, which is a schematic sectional view of the catheter shown in FIG. 2 taken through its axis of symmetry in accordance with an embodiment of the invention.

Reference is now made to FIG. 3, which is a schematic sectional view of the distal end 37 (FIG. 2) taken through the axis of symmetry 39 in accordance with an embodiment of the invention. Each microelectrode 45 receives at least one conductive wire 49. Similarly, each microelectrode 47 receives at least one conductive wire 49. The conductive wires 49 are typically insulated so that they are electrically isolated from the wall of the distal end 37. A shield 51, described in further detail below, surrounds the conductive wire 49 leading from the microelectrode 47. In each case, the conductive wires 49 are connected to the microelectrodes 45, 47, typically by soldering and/or welding. Each conductive wire 49 is conveyed circuitry in the console 24 (FIG. 1), enabling potentials generated at the different microelectrodes to be measured.

Further details of the distal end 37 are found in commonly assigned copending application Ser. No. 14/279,682, which is herein incorporated by reference.

Figure 4:
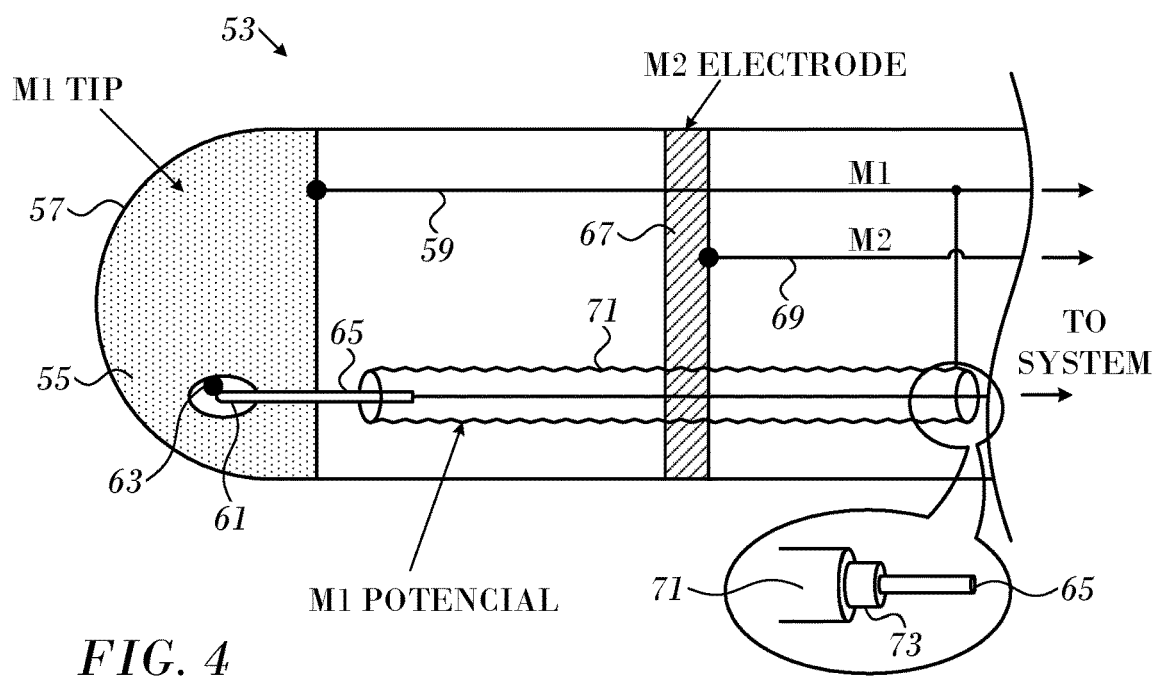
FIG. 4 is a schematic diagram of an embodiment of the distal segment of an ablation catheter, in accordance with an embodiment of the invention.

Reference is now made to FIG. 4, which is a schematic diagram of an embodiment of the distal segment of an ablation catheter 53 in accordance with an embodiment of the invention. The catheter 53 has an ablation electrode 55 (M1) at tip 57 connected to a wire 59 that supplies power from a system console (not shown). A microelectrode 61 on the ablation electrode 55 can be a sensing electrode, e.g., by linkage to a thermocouple 63. The microelectrode 61 is connected to the system console by a wire lead 65. A ring electrode 67 (M2) may provide other sensor information, e.g., an electrogram, and is connected to the system console by a wire 69. An electrical shield 71, e.g., a coaxial layer, surrounds the wire lead 65, and may be separated from the wire lead 65 by a dielectric layer 73. An optional external insulating jacket (not shown) may overly the electrical shield 71.

Figure 5:
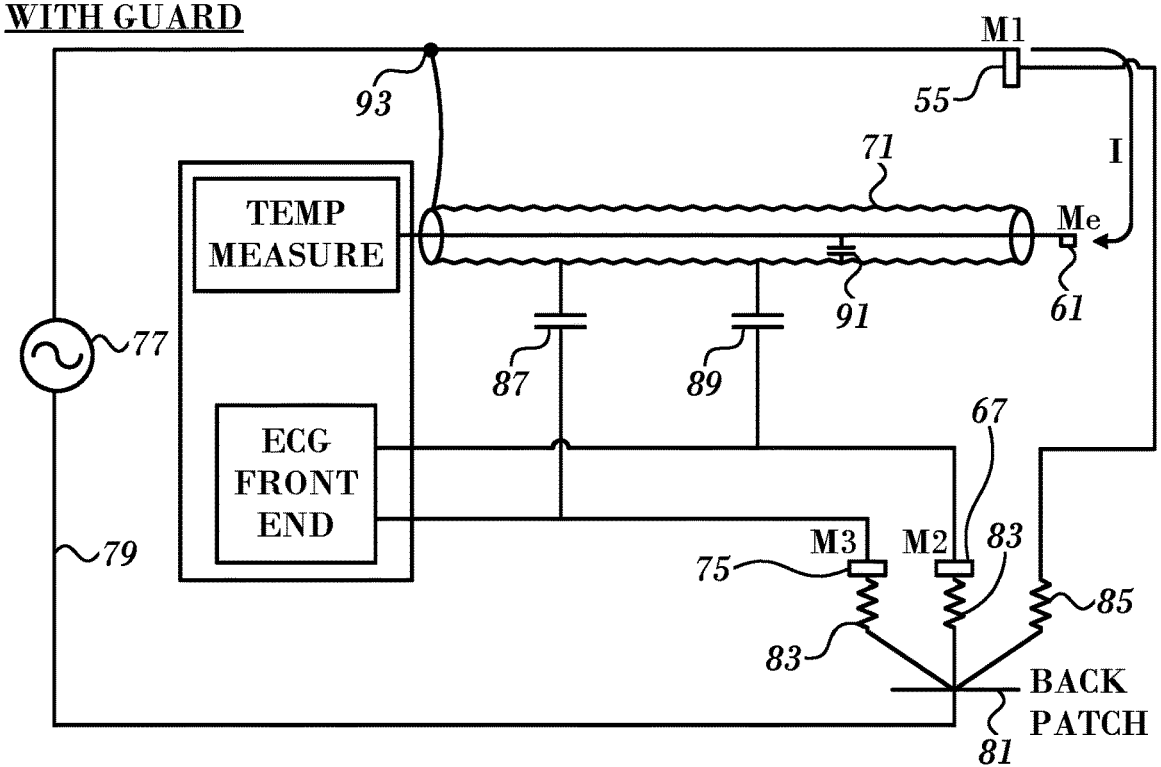
FIG. 5 is an electrical schematic of the arrangement shown in FIG. 4 in accordance with an embodiment of the invention showing respective parasitic current distribution because of the ablation signal.

Reference is now made to FIG. 5, which is an electrical schematic of the arrangement shown in FIG. 4 in accordance with an embodiment of the invention. ECG electrodes 67, 75 and ablation electrode 55 mounted on the ablation catheter shaft are connected to a power generator 77 via generator circuit 79 via a back patch 81 through the patient body. Resistances of the patient's body are represented by resistors 83 between the ECG electrodes 67, 75 and the back patch 81. Resistance of the patient's body between the ablation electrode 55 and the back patch 81 is represented by resistor 85. The back patch 81 may be implemented by a conventional skin patch that is connectable to the patient's body. Parasitic capacitances 87, 89 of ECG electrodes 67, 75 and parasitic capacitance 91 of the microelectrode 61 are separated by the electrical shield 71 connected to the generator circuit 79 via the electrical junction 93. The electrical shield 71 provides an envelope with potential equal to the potential of ablation electrode 55 (M1) so that the differential potential between ablation electrode 55 (M1) and microelectrode 61 and hence the current flowing therebetween is minimized. Interference with the signal produced by microelectrode 61 is consequently minimized. Leakage current from ECG electrodes 67, 75 due to parasitic capacitances 87, 89 is supplied by the ablation electrode 55 (ml) through junction 93 and the electrical shield 71 (and not by microelectrode 61).

Figure 6:
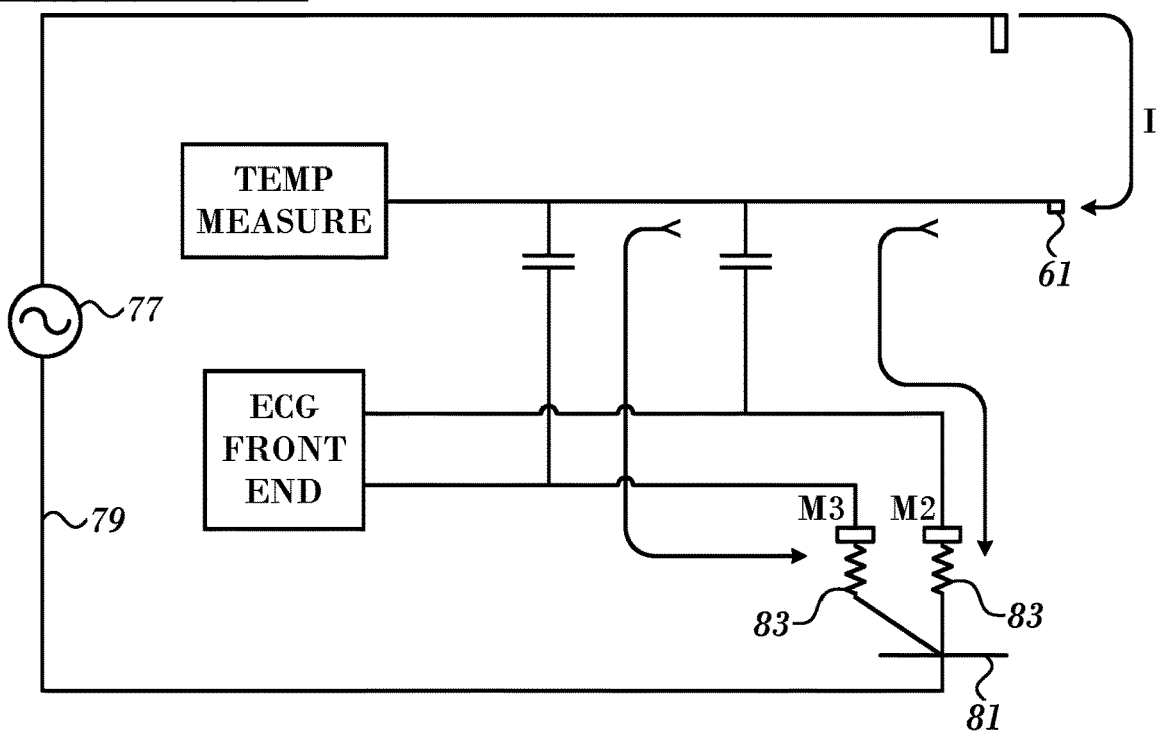
FIG. 6 is an electrical schematic showing a version of the arrangement without the guard protection in accordance with the prior art.

Reference is now made to FIG. 6, which is an electrical schematic showing a version of the elements of the circuit shown in FIG. 5, in accordance with the prior art. In the absence of the electrical shield shown in FIG. 5 capacitive leakage current can flow between the microelectrode and the afferent limb of the generator circuit via the resistors 83 (representing the patient's body) and the back patch 81. This can accordingly cause microablation on microelectrode 61 and distort readings taken from the microelectrode 61, e.g., temperature measurements via the linked thermocouple 63 (FIG. 4).

It will be appreciated by persons skilled in the art that the present invention is not limited to what has been particularly shown and described hereinabove. Rather, the scope of the present invention includes both combinations and sub-combinations of the various features described hereinabove, as well as variations and modifications thereof that are not in the prior art, which would occur to persons skilled in the art upon reading the foregoing description.

The invention claimed is:

1. A method, comprising the steps of:
    inserting a Flexible catheter into a heart of a living subject, the catheter having a distal segment, an ablation electrode disposed at the distal segment, the ablation electrode having an external surface, a cavity formed in the external surface, a microelectrode configured to fit into the cavity
    a conductive wire lead to connecting the microelectrode to receiving circuitry, and
    an electrical shield surrounding the conductive wire lead, the electrical shield being electrically connected directly to an ablation electrode conductive wire lead via a wire and configured to equalize potentials between the ablation electrode and the microelectrode to minimize capacitance leakage current flow;
    contacting the ablation electrode with a target tissue in the heart; and while receiving signals from the microelectrode in the receiving circuitry energizing the ablation electrode to ablate the target tissue.

2. The method according to claim 1, further comprising the steps of: connecting a power generator to the ablation electrode and the electrical shield in a generator circuit; and connecting a back patch electrode to the subject and to the generator circuit.

3. The method according to claim 1, wherein the electrical shield comprises:
   a coaxial layer; and
   a dielectric layer disposed between the coaxial layer and the conductive wire lead.

4. The method according to claim 3, wherein the electrical shield further comprises an insulating jacket that overlies the coaxial layer.

5. The method according to claim 1, wherein the external surface of the ablation electrode has a curvature, and the microelectrode is contoured, located and oriented to conform to the curvature.

6. The method according to claim 1, wherein the ablation electrode has a cylindrical portion, wherein the cavity comprises a plurality of cavities formed in the cylindrical portion.

7. The method according to claim 1, wherein the ablation electrode has a distal annular portion, wherein the cavity comprises a plurality of cavities formed in the distal annular portion and wherein the microelectrode comprises a plurality of microelectrodes disposed therein.

8. The method according to claim 1, wherein the microelectrode is linked to a thermocouple, wherein the thermocouple provides a signal representative of a temperature of the microelectrode.

\* \* \* \* \*